United States Patent [19]
Craddock et al.

[11] 3,989,747
[45] Nov. 2, 1976

[54] PRODUCTION OF PROPIONIC ACID

[75] Inventors: John H. Craddock, Ballwin; James F. Roth, St. Louis; Arnold Hershman, St. Louis; Frank E. Paulik, St. Louis, all of Mo.

[73] Assignee: Monsanto Company, St. Louis, Mo.

[22] Filed: May 28, 1974

[21] Appl. No.: 473,464

Related U.S. Application Data

[63] Continuation-in-part of Ser. No. 59,410, July 30, 1970, abandoned, which is a continuation-in-part of Ser. No. 752,746, Aug. 15, 1968, Pat. No. 3,579,552.

[52] U.S. Cl. .......................... 260/533 AN; 252/441
[51] Int. Cl.² ......................................... C07C 51/14
[58] Field of Search ............................. 260/533 AN

[56] References Cited
UNITED STATES PATENTS

| | | |
|---|---|---|
| 2,739,169 | 5/1956 | Hagemeyer .................. 260/533 AN |
| 3,065,242 | 11/1962 | Alderson ...................... 260/533 AN |
| 3,509,209 | 4/1970 | Fenton .......................... 260/533 AN |
| 3,579,552 | 5/1971 | Croddock ..................... 260/533 AN |
| 3,637,833 | 11/1972 | Fenton .......................... 260/533 AN |

FOREIGN PATENTS OR APPLICATIONS

| | | |
|---|---|---|
| 737,535 | 2/1970 | Belgium ....................... 260/533 AN |

Primary Examiner—Anton H. Sutto

[57] ABSTRACT

The present invention relates to an improved one-step process for the preparation of propionic acid, specifically by the reaction of ethylene with carbon monoxide and water at mild pressure, in the presence of catalyst compositions essentially comprising critical proportions of rhodium components with a bromide promoter. Under these reaction conditions, the process is catalytic both with respect to the rhodium and the bromide components.

8 Claims, 1 Drawing Figure

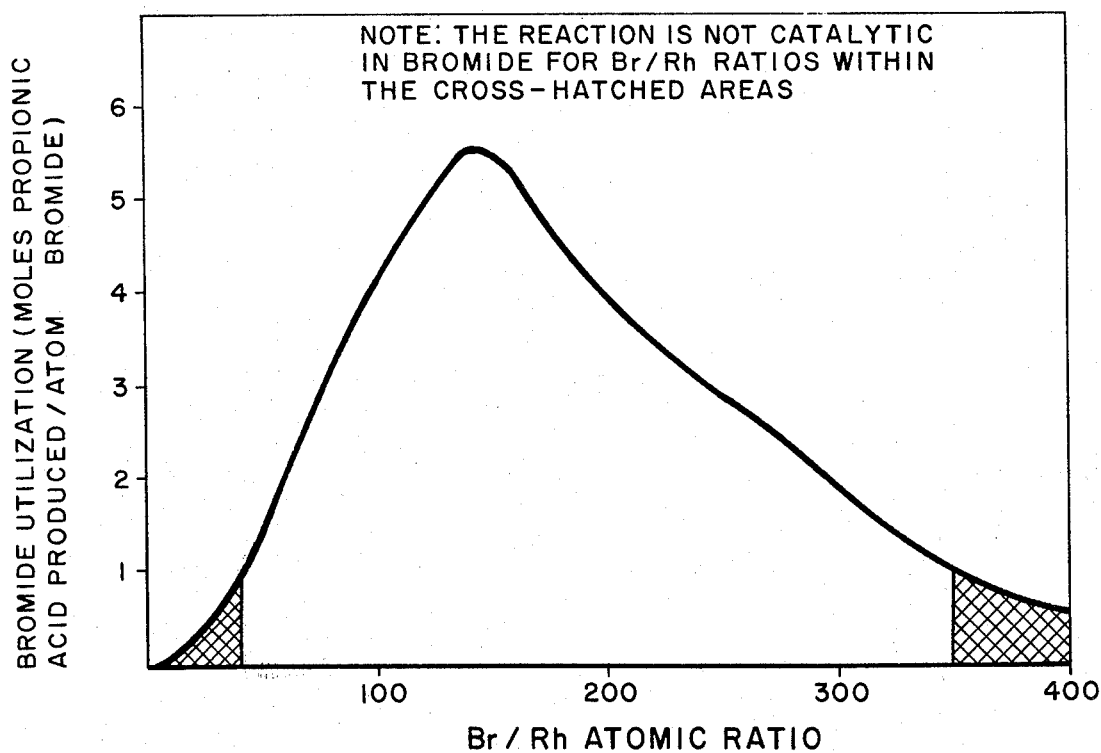

PRODUCTION OF PROPIONIC ACID

This application is a continuation-in-part of Ser. No. 59,410 filed July 30, 1970, now abandoned, which is a continuation-in-part of Ser. No. 752,746, filed Aug. 15, 1968, now U.S. Pat. No. 3,579,552.

This invention relates to an improved process for the production of propionic acid. More particularly, it relates to a one-step process for the reaction of ethylene with carbon monoxide and water in the presence of catalyst compositions essentially comprising critical ratios of rhodium compounds and complexes and bromide to yield propionic acid selectively and efficiently at mild pressure. Through control of the atomic ratio of the bromide to the rhodium component, the system is catalytic both with respect to the metal and the bromide components.

The discovery of the role of critical bromide/rhodium atomic ratio in producing a process with vastly superior performance is clearly unexpected from the prior art. A number of metals are reported to catalyze the conversion of olefins to carboxylic acids employing halides in the system. Generally these halides are not a catalytic component of the system but are only present in stoichiometric proportions to the product formed (i.e. the production of carboxylic acid is catalytic in the metal component but non-catalytic in the halide component). Consequently it is necessary to use very large amounts of expensive halogens, since the halogen is only used once, instead of being constantly re-used as in a true catalytic process. Unlike those prior art systems, the present invention is required to be a two component catalyst system (i.e. rhodium and bromide) and the production of carboxylic acids is catalytic in both components of the catalyst system (e.g. a single atom of either the bromine or of the metal is utilized repeatedly in many turnovers instead of being used only once or less to form the propionic acid product). Furthermore, none of these prior art teachings recognized or indicated in their examples the large process advantages obtained by maintaining control of the bromide to metal ratio within the critical ratios now discovered.

In this connection, it would be expected that with the halide being a promoter to the reaction, higher concentrations of the promoter would be preferable. As is shown below such is not the case and reactions run at the high halide/metal ratios are not only expensive in the use of the halide but are not even catalytic in the halide. The excess halide beyond that taught by the present critical ratio instead of promoting the desired reaction slows the reaction.

The previous metal catalyzed synthesis of carboxylic acids from olefins, carbon monoxide and water promoted by or in the presence of halide has mostly employed chloride as the halide of preference usually as aqueous hydrochloric acid. It might be expected that bromide will function equivalent to chloride but the prior art examples essentially all employ chloride. The metal catalysts employed are most often nickel, cobalt or iron; however, more recently the noble metals of Group VIII particularly palladium and rhodium have been successfully employed as catalysts in the synthesis of carboxylic acids via hydrocarboxylation of olefins. For example in a recent patent, U.S. Pat. No. 3,637,833, carboxylic acids were prepared from olefins in the presence of a rhodium catalyst. The halide present in all the examples was concentrated hydrochloric acid. The patentee failed to discuss halide/metal ratio and his examples all employ a high atomic ratio of chloride/rhodium of 230/1. The table below:

| EXAMPLE | ATOMS OR MOLES OF CHLORIDE | MOLES OF PROPIONIC ACID PRODUCED | HALIDE UTILIZATION (A figure greater than 1.0 indicates catalytic reaction with respect to halide) |
|---|---|---|---|
| 1 | 0.3 | 0.027 | 0.09 |
| 2 | 0.3 | 0.23 | 0.77 |
| 3 | 0.3 | 0.13 | 0.43 | taken from the examples in columns 2 and 3 of the above patent establishes that in no example is the patentee's carbonylation reaction to propionic acid catalytic in the halide component.

In contrast as demonstrated in the examples of the present case, at the critical bromide/rhodium ratios of the present invention, bromide utilizations of 5 or greater are achieved establishing that the production of propionic acid is catalytic in the bromide component (and also in the rhodium component). The above U.S. Pat. No. 3,637,833 while catalytic in propionic acid production relative to the rhodium component is considerably less than stoichiometric, and consequently not catalytic, in his chloride utilization by failure to recognize the concept of critical bromide/rhodium ratio.

Another U.S. Pat. No. 3,065,242 also employed halides and carbonyls of group VIII noble metals as catalysts in the process of preparing acyl halide, which in a second step were transformed to the corresponding carboxylic acids and lactones. The halide was a hydrogen halide selected from hydrogen bromide and hydrogen chloride. Examples are shown in columns 2 through 4 of that patent. The halide to metal ratio is high in all eleven examples, either 250 or 340 halides per metal (atomic ratio). As with U.S. Pat. No. 3,637,833 discussed above, at these high ratios, the latter U.S. Pat. No. 3,065,242 does not achieve a catalytic reaction in the total halide present. The latter patent in all its examples do demonstrate a catalytic reaction in the halide, carbonyl, or chelate of the Group VIII noble metal, calculated as the stoichiometric compound, but does not demonstrate a catalytic reaction in the halide component including the hydrogen halide added separately to the reactor. By control of the critical ratio as shown in the examples herein the applicants are catalytic in both the rhodium and in the total bromide, including that added separately to the reactor. The latter U.S. Pat. No. 3,065,242 lists the yield of carboxylic acid based on the hydrogen halide charged to the reactor (e.g. example 1 of this patent states that the total yield of propionic acid isolated in this case is 90%). For U.S. Pat. No. 3,065,242 to have a catalytic reaction in the hydrogen halide charged to the reactor the yield would have to exceed 100%. A yield lower than 100% is only stoichiometric in the hydrogen halide component; e.g. not catalytic. "Yield" in this latter patent corresponds to 100 times the moles of product formed per atom (or mole) of halide used in the discussion of former U.S. Pat. No. 3,637,833 above. In no example of U.S. Pat. No. 3,065,242 does the yield of product based on the hydrogen halide exceed 100%; i.e. in no example is the patentee catalytic in the halide component. This patentee failed to understand the concept of critical bromide to rhodium ratio and therefore operated above the present range with the result that in U.S. Pat. No. 3,065,242 there is only generated a stoichiometric reaction in his halide component. As the patentee pointed out a second process step is required to convert the acyl halide to the carboxylic acids.

In a later patent (U.S. Pat. No. 3,020,314) employment is made of Group VIII noble metal catalysts. In this case however the patentee did not operate at the high halide/metal ratios of the earlier U.S. Pat. No. 3,065,242. In general the only halide present in U.S. Pat. No. 3,070,314 is that with the metal salt (i.e. 3 halides/metal as in the stoichiometric formula, e.g. $RhCl_3$). In addition to the metal halide, a compound from Group V must also be present in every instance. The product produced from the 3 component catalyst system of U.S. Pat. No. 3,070,314 above not operated at the critical halide/metal ratios of the processes of the present invention, is not carboxylic acids but alcohols and aldehydes and ketones. This demonstrates another advantage of the critical control of bromide/rhodium ratios as taught herein. By such control the present invention achieves a very specific and selective reaction to propionic acid unlike U.S. Pat. No. 3,020,314 above in which alcohols, aldehydes and ketones are produced.

To further demonstrate the unpredictability of the concept of the critical bromide/rhodium atomic ratio as applied to the production of propionic acid from ethylene, carbon monoxide and water reference is made to another patent, U.S. Pat. No. 3,509,209. In this patent, examples are shown only for palladium as the catalytic metal although other Group VIII noble metals are taught as catalysts. The reaction is performed in the presence of aqueous hydrohalic acids such as aqueous hydrochloric or aqueous hydrobromic acid. Nine examples are shown in columns 4 through 6 of this U.S. Pat. No. 3,509,209 patent. The halide/metal atomic ratios in the examples of this patent varies from 50 to 100/1, ratios within the range taught in the processes of the present invention. It would therefore be expected that the latter U.S. Pat. No. 3,509,209 patent might achieve the superior process advantages described herein. Such is not the case because with respect to the concept of critical bromide/rhodium ratios all halides and all metals are not equivalent. This U.S. Pat. No. 3,509,209 employs palladium rather than the rhodium of the present invention. The best yield achieved in U.S. Pat. No. 3,509,209 based on the halide component, is 0.4 moles of product formed/atom (or mole) of halide (e.g. in Example 5). In the other eight examples the moles of product formed per atom of chloride (or bromide) varies from 0.09 to 0.25. These results establish that the process of U.S. Pat. No. 3,509,209 while catalytic relative to the palladium component is not even stoichiometric and consequently far from catalytic in the halide component. In contrast, in the claimed critical bromide/rhodium ratios the applicants results show that propionic acid production is catalytic in both the rhodium and bromide components of the catalyst system.

For example the applicants at a ratio of 90 Br/Rh produce 3.6 moles of propionic acid per atom of bromide fed (present example 3). This result corresponds to a turnover of bromide greater than 1 (e.g. a value of 3.6) establishing the catalytic nature of the reaction relative to the bromide component while the last patent above U.S. Pat. No. 3,509,209 only demonstrates a turnover from 0.09 to 0.4 which is far less than required to establish the catalytic nature of the reaction relative to the halide component.

Other investigators reported in the prior art have also equated many metals of Group VIII as catalysts for the production of organic acids. U.S. Pat. No. 2,739,169 has taught the equivalence of several Group VIII noble metals (e.g. Pd, Ru, Ir) to the iron subgroup, Fe, Ni and Co. However the examples and claims of this patent are specific only to Fe, Ni and Co. In columns 3 through 7 of the patent 19 examples are shown. In no example does the halide to metal ratio exceed 2.0. This ratio is below the bromide/rhodium ratio for which the ethylene carbonylation to propionic acid, as shown herein, is effective. This demonstrates again the non-equivalence of the metal component of the catalyst system. It is noted that the operating conditions of the examples of U.S. Pat. No. 2,739,169 are much more severe than those for the rhodium-bromide catalyst system. Temperatures in the range of 300° C are employed at pressures of in the range of 5000 psi at the low ratio of halide to metal of this last patent. For the improved processes catalyzed at the applicants critical bromide/rhodium ratio the preferred temperature range is 125° to 225° C and the preferred carbon monoxide partial pressure is 25 psia to 500 psia.

STATEMENT OF THE INVENTION

It is, therefore, an object of the present invention to overcome the above disadvantages and thus provide an improved and more economically and commercially feasible one-step carbonylation process for the production of propionic acid from ethylene, in liquid phase and vapor phase processes at low pressure.

Another object of this invention is to provide a more reactive and more stable carbonylation catalyst composition than has been heretofore described in the prior art. A system catalytic in both the metal and bromide components which better utilizes the expensive catalyst and minimizes corrosion and handling losses caused by high halide concentration. Chlorides are especially severe as to corrosivity.

Still another object of the present invention is to provide a more selective and more reactive carbonylation catalyst composition for the production of propionic acid from ethylene.

Another object of the present invention is to provide a carbonylation catalyst composition which results in the production of a higher yield of the desired carboxylic acid with no substantial formation of ethers, aldehydes, ketones, lactones, higher carbon number carboxylic acids and alcohols, carbon dioxide, methane, water and other undesirable by-products.

Still another object of the present invention is the provision of an improved carbonylation process enabling the efficient and selective production of propionic acid by reaction of ethylene with carbon monoxide and water at low pressure in the presence of an improved and more stable catalyst, thus enabling the use of lower catalyst concentration, lower temperature, and shorter contact time than has been generally possible heretofore.

In accordance with the present invention superior yields of propionic acid are obtained by reaction of ethylene in the liquid phase or vapor phase with carbon monoxide and water at temperatures from about 50° to 300° C, preferably 125° to 225° C, and at partial pressures of carbon monoxide from 1 psia to 1500 psia, preferably 25 psia to 500 psia although higher pressure may be employed, in the presence of a catalyst system which is catalytic both with respect to the metal and bromide component and which is comprised of a rhodium containing component, and a bromide component used in critical atomic ratios defined herein. The present process is particularly advantageous at lower pressures, although higher pressures may also be used.

DESCRIPTION OF THE PREFERRED EMBODIMENTS

For purposes of the present invention, the catalyst system essentially includes both metal and halogen components. The metal component is rhodium and the halogen component is bromine. Generally, the metal component of the catalyst system of the present invention is believed to be present in the form of a coordination compound of rhodium with a halogen component providing at least one of the ligands of such coordination compound. In addition to the metal and halogen, in the process of the present invention, these coordination compounds also generally include carbon monoxide ligands thereby forming such compounds or complexes of rhodium such as $[Rh(CO)_2Br]_2$. Other moieties may be present if desired. Generally it is preferred that the catalyst system contain as a promoting component, an excess of bromide over that present as ligands in the coordination compound. The terms "coordination compound" and "coordination complex" used throughout this specification means a compound or complex formed by combination of one or more electronically rich molecules or atoms capable of independent existence with one or more electronically poor molecules or atoms, each of which may also be capable of independent existence.

The essential metal and bromide components of the catalyst system of the present invention may be provided by introducing into the reaction zone a coordination compound of rhodium containing bromide ligands or may be provided by introducing into the reaction zone separately a metal compound and a bromide compound. Among the materials which may be charged to the reaction zone to provide the metal component of the catalyst system of the present invention are rhodium metal, rhodium salts and oxides, organo rhodium compounds, coordination compounds of rhodium and the like. Specific examples of materials capable of providing the metal constituent of the catalyst system of the present invention may be taken from the following non-limiting partial list of suitable materials. Chemical and/or physical treatment of the metal precursor may be desirable as discussed below, in order to render the rhodium moiety in the proper valence state and ligand environment. For example, rhodium complexes containing stable chelating ligands, such as trisacetylacetonato rhodium, may be treated chemically to remove or destroy the bidentate chelate ligands in order that transformation to the proper valence state and monodentate ligand configuration can be accomplished.

| | |
|---|---|
| Rh metal | $[(n-C_4H_9)N] [Rh(CO)_2X_2]$ where $X=Cl^-, Br^-$ $I^-$ |
| $RhCl_3$ | $[(n-C_4H_9)_4As]_2[Rh_2(CO)_2Y_4]$ where $Y=Br^-$, $I^-$ |
| $RhBr_3$ | $[(n-C_4H_9)_4P] [Rh(CO)I_4]$ |
| $RhI_3$ | $Rh[(C_6H_5)_3P]_2(CO)Br$ |
| $RhCl_3 \cdot 3H_2O$ | $Rh[(n-C_4H_9)_3P]_2(CO)Br$ |
| $RhBr_3 \cdot 3H_2O$ | $Rh[(n-C_4H_9)_3P]_2(CO)I$ |
| $Rh_2(CO)_4Cl_2$ | $RhBr[(C_6H_5)_3P]_3$ |
| $Rh_2(CO)_4Br_2$ | $RhI[(C_6H_5)_3P]_3$ |
| $Rh_2(CO)_4I_2$ | $RhCl[(C_6H_5)_3P]_3$ |
| $Rh_2(CO)_8$ | $RhCl[(C_6H_5)_3P]_3H_2$ |
| $Rh[(C_6H_5)_3P]_2(CO)I$ | $[(C_6H_5)_3P]_3Rh(CO)H$ |
| $Rh[(C_6H_5)_3P]_2(CO)Cl$ | $Rh[(C_2H_4)_2Cl]_2$ |
| $RhCl[(C_6H_5)_3P]_2(CH_3I)_2$ | $K_4Rh_2Cl_2(SnCl_3)_4$ |
| $Rh(SnCl_3)[(C_6H_5)_3P]_3$ | $K_4Rh_2Br_2(SnBr_3)_4$ |
| $RhCl(CO)[(C_6H_5)_3As]_2$ | $K_4Rh_2I_2(SnI_3)_4$ |
| $RhI(CO)[(C_6H_5)_3Sb]_2$ | $Rh_2O_3$ |
| | $Rh(NO_3)_3$ |

With those materials listed above as capable of providing the metal component which do not contain a bromide component, it will be necessary to introduce into the reaction zone such a bromide component. For example, if the rhodium component introduced is rhodium metal or $Rh_2O_3$, it will be necessary to also introduce a bromide component such as ethyl bromide, hydrogen, bromide, bromine or the like.

As noted above, while the bromide component of the catalyst system may be in combined form with the rhodium as for instance, as one or more ligands in a coordination compound, it generally is preferred to have an excess of bromide present in the catalyst system as a promoting component. By excess is meant an amount of bromide greater than 2 atoms of halogen per atom of metal in the catalyst system. This promoting component of the catalyst system consists of a bromine and/or bromide compound such as hydrogen bromide, alkyl or aryl bromide, metal bromide, ammonium bromide, phosphinium bromide, arsonium bromide, stibonium bromide and the like. The bromide of the promoting component may be the same or different from that already present as ligands in the coordination compound of rhodium. Accordingly, suitable bromide providing or promoting components may be selected from the following list of bromine and/or bromide containing compounds.

| | | | |
|---|---|---|---|
| RBr | where | R=any alkyl-or aryl-group | e.g. $CH_3Br$, $C_6H_5Br$ etc. |
| $Br_2$ | | | |
| HBr | | | |
| RCBr ‖ O | where | R=any alkyl-or aryl-group | e.g. $CH_3CBr$ etc. ‖ O |
| $R_4MBr$, $R_4MBr_3$, or $R_3MBr_2$ | | | |
| | where | R-Hydrogen or any alkyl- | e.g., $NH_4Br$, $PH_3Br_2$ |
| | | M=N, P, As, or Sb | $(C_6H_5)_3PBr_2$ and/or combinations of R, M, and Br |

It has been discovered that critical ratios of bromide to active metal catalyst, expressed as atoms of bromide to atoms of metal atom in the active portion of the catalytic systems, exist. Within the range of these critical ratios, very reactive and selective ethylene carbonylation catalyst systems (catalytic in both components) comprised of bromine and an active metal component provided by rhodium precursors, are found that function very efficiently at milder temperatures and pressures than were heretofore possible. The optimum critical atomic ratio of bromide atoms to rhodium atoms is in the range of 40:1 to about 350:1 for reactions of ethylene, carbon monoxide and water in aqueous carboxylic acid solvent systems. More preferably the range of critical ratios of halide to metal atom employed are 80:1 to 250:1.

Outside the range of critical ratios of bromide to metal atoms, particularly at the higher bromide levels, the reactiion efficiency and yield is drastically reduced and the reaction ceases to be catalytic in the bromide component. For example at the higher halide levels, significantly higher partial pressure of carbon monoxide is required for the reaction to proceed at an appreciable rate. Also at the higher bromide levels, i.e. higher ratio of halide to metal, the specificity to carboxylic acid product, i.e. propionic acid, is significantly reduced and numerous oxygenated by-products such as ketones, lactones, aldehydes, etc. are formed including oxygenated derivatives of ethylene and oligomers of higher molecular weight.

The exact nature of the optimum critical ratio of promoter halogen to metal atom of the catalytic system has not been completely elucidated and may vary as a function of other reaction parameters including solvent composition, absolute concentration of catalyst components, e.g., metal and halogen constituents, and water concentrations.

Generally, it is preferred that the process of the present invention be carried out in an acidic reaction medium. For purposes of the present invention, an acidic reaction medium is defined as one in which an alkyl halide is present or will be formed. For example, when the feed is ethylene, the alkyl halide will be the ethyl bromide. Such alkyl halide may be added to the reaction medium as such or may be formed in situ within the reaction medium from the ethylene feed and the bromide present in the catalyst system. The reaction medium is considered acidic when under reaction conditions as herein set forth, at least 10% by wt. of the total halogen in the system is present as the alkyl halide. It is preferred, however, that at least 20% by wt. of the total bromide in the system is present as the alkyl bromide.

The preparation of the active catalyst complex which includes both metal and bromide components may be accomplished by a variety of methods. However, it is thought that a substantial part of the precursor rhodium component is converted to the monovalent state during the preparative treatment. In general, in the process of this invention, it is convenient to preform the active carbonylation catalyst system which contains both metal and bromide components. For example, to prepare the catalyst system, the metal component of the catalyst system, e.g., finely divided rhodium metal (powder), a simple rhodium salt or compound as a precursor is dissolved in a suitable medium, and carbon monoxide is bubbled through the above solution, preferably while maintaining gentle heating and stirring of the solution. Then a solution of the desired bromide source is added to form an active catalytic solution containing the necessary metal and bromide components.

Generally, the active catalyst containing the rhodium and bromide components of the catalyst system of this invention may be preformed prior to charging the reactor, or it may be formed in situ in the reactor as discussed above. For example, to prepare the catalyst system, the first component of the catalyst system, e.g., a rhodium salt such as $RhBr_3 \cdot 3H_2O$ is dissolved in a suitable solvent such as 2-methoxyethanol. Subsequently, carbon monoxide is bubbled through the solution where an intermediate, such as the dimer $[Rh(CO)_2Br]_2$, is produced wherein the rhodium is in the monovalent state. The second component is, for example, added to the above solution; e.g., as aqueous HBr, elemental bromine, alkyl bromide (with alkyl radicals of 1 to 30 carbon atoms) or other bromide containing compounds.

Alternatively, a rhodium precursor, e.g., $RhBr_3 \cdot 3H_2O$ or $Rh_2O_3 \cdot 5H_2O$ may be dissolved in 2-methoxyethanol containing a dilute aqueous acid, e.g., HBr, acetic acid, etc., as solvent. Then the solution of the rhodium compound is heated, for example to 60° – 80° C, or in general at a temperature below the boiling point of the solvent, with stirring. A reducing agent such as carbon monoxide is bubbled through the said solution to obtain the rhodium component at least in part in the monovalent state. Subsequently, the bromide component is added as described herein, although the bromide containing component may also be added first.

Another embodiment of the present invention employs compounds of monovalent rhodium initially, wherein the transformation to active catalyst may not involve a change of valence. For example, monovalent rhodium compounds such as $[Rh(C_6H_5)_3P]_2(CO)Cl$, and $[Rh(CO)_2Cl]_2$ etc. are dissolved in a suitable solvent that is preferably warmed and stirred. Subsequent addition of a solution of the bromide, e.g., alkyl bromide, elemental bromine, aqueous HBr etc., results in formation of an active carbonylation catalyst solution.

Alternate embodiments of the present invention include use of other rhodium components in various oxidation states and ligand environments, e.g., metals (zero valence state), rhodium salts, e.g., $RhCl_3$ (+3 valence state), other compounds, e.g., rhodium acetylacetonate (+3 valence state), etc.; with suitable chemical reagents to accomplish the desired transformation of the precursor to an active catalytic complex species. Such reagents include reducing agents, e.g., hydrogen, carbon monoxide, hydrazine, formic acid, phenylhydrazine, etc.; and oxidizing agents, e.g., elemental halogens ($I_2$ or $Br_2$), mineral acids (HCl, HBr, $HNO_3$, HI), peroxides ($H_2O_2$, cumene hydroperoxide, etc.).

This catalytic solution containing the necessary metal and bromide components is then ready for use as discussed above, and may be employed as a liquid phase or vapor phase catalyst. As discussed above it is beneficial and desirable to have the concentration of the second component of the catalyst system, for example, ethyl bromide, HBr or $Br_2$, in excess of that required to form a stoichiometric compound such as described above. In the same way the two components, e.g., a metal compound containing the bromide component may be provided in a single molecule by beginning with metal tribromide as the catalyst precursor for the reaction of ethylene with carbon monoxide and water to produce propionic acid. The present discussion is based upon the catalyst precursors as charged. The ultimate nature of the catalyst as modified by reaction conditions, and the presence of promoters and reactants has not been completely elucidated. However, it has been found that the use of the components as described herein provides a highly superior catalyst and process for the production of propionic acid.

As discussed above the reaction system consists of catalytic amounts of bromide and rhodium components charged in critical ratios as defined herein. The use of catalytic quantities of these two components within critical atomic ratios in the present invention is in contradistinction to prior art processes which employed certain halide promoters in substantially stoichiometric proportion to the olefinic feed, e.g., 1 mole of halide per mole (equivalent) of olefin. As discussed below the critical proportions of halide-metal catalyst system of the present invention results in significantly higher yields of carboxylic acid of the order to 1000 to 1,000,000 mole % or more based upon bromide and/or metal component charged.

The liquid reaction medium employed may be any solvent compatible with the catalyst system and may include pure olefins or saturated and unsaturated hydrocarbons, e.g., benzene, decane, eicosane, etc. Mixtures thereof with the desired carboxylic acid and/or other carboxylic acids such an nonanoic acid may be used.

The preferred solvent system employed in the present invention in order to achieve a high proportion of propionic acid, rather than the acid anhydride as the product, is based upon the use of an aqueous solution of a carboxylic acid having 2 to 20 carbon atoms as the solvent medium. It has been found that water is essential in the use of the catalyst system.

Although the ethylene-water reaction stoichiometry is 1:1 the preferred catalyst system containing the critical proportions of bromide and rhodium metal component is comprised of an aqueous solution of the carboxylic acid, which may be the same or different from the propionic acid product as discussed above, wherein the water concentration is from 1 to 25% by weight of the catalyst solution.

For example in a continuous process a stoichiometric quantity of water equivalent to the number of moles of ethylene reacted (or propionic acid produced) is added continuously to maintain the necessary water concentration of the catalyst solution.

The catalyst system of the present invention is unique in comparison to earlier work in that it does not require the use of anhydrous or highly concentrated mineral acid solutions. Furthermore the present aqueous catalyst system permits the use of halogen sources such as alkyl halides e.g. ethyl bromide in place of the highly corrosive mineral acids such as concentrated HBr. These factors serve greatly to reduce the corrosivity of the reaction system.

The present invention is based upon the production of propionic acid by the reaction of ethylene, carbon monoxide and water.

In accordance with the present invention, the carbonylation reaction may be carried out by intimately contacting gaseous ethylene with gaseous carbon monoxide and water (vapor or liquid) in a liquid phase containing the catalyst system prepared from rhodium precursors and a bromine containing component, such as ethyl bromide, under conditions of temperature and pressure suitable as described herein to form the carbonylation product. The temperature accordingly will be in the range of 50° to 300° C with the preferred range being 125° to 225° C. Partial pressures of carbon monoxide of the order of 1 psia to 1500 psia may be employed; however, 25 psia to 500 psia carbon monoxide partial pressure is generally preferred. Higher pressures may be used if desired under appropriate conditions.

Alternatively, propionic acid may be produced if desired via reaction of ethylene with carbon monoxide and water in the vapor phase over the rhodium containing catalyst systems described above, dispersed upon inert supports. Such a catalyst system may be operated as a conventional fixed bed catalytic reactor. For example, ethylene, aqueous hydrogen bromide, and carbon monoxide may be passed over a catalyst system consisting, for example, of $[Rh(CO)_2Br]_2$ dispersed on an inert support material such as alundum, activated carbon, clays, alumina, silica-alumina, and ceramics, etc., in a fixed bed reactor maintained at elevated temperature and pressure, as described above, to produce propionic acid in high yields. However, use of a liquid reaction medium is preferred in the process of this invention using dissolved or dispersed active catalytic and promoter components.

A typical carbonylation reaction selective to carboxylic acid requires at least 1 mole of carbon monoxide and 1 mole of water per mole (equivalent) of ethylene reacted. Excess of carbon monoxide and water over the aforesaid stoichiometric amounts, however, may be present. Carbon monoxide streams containing inert impurities such as carbon dioxide, methane, nitrogen, noble gases and paraffinic hydrocarbons having from 1 to 4 carbon atoms, may be employed, if desired, for example from an available plant gas stream, with no ill effect; however, in such cases total reactor pressure will have to be increased to maintain a desired carbon monoxide partial pressure. The concentration of carbon monoxide in the feed gas mixture is from 1 vol. % to 99.9 vol. %, a preferred range being from 10 vol. % to 99.9 vol. %.

The reaction rate is dependent upon catalyst concentration and temperature. Concentrations of the rhodium compound or the first component of the catalyst system in the liquid phase, between $10^{-6}$ moles/liter and $10^{-1}$ moles/liter, are normally employed, with the preferred range being $10^{-4}$ moles/liter to $10^{-2}$ moles/liter. Higher concentrations even to the extent of 1 mole/liter may, however, be used if desired. Higher temperatures also favor higher reaction rates.

The concentration of the bromide component of the catalyst system may vary widely over the broad concentration range of $10^{-6}$ moles/liter to 18 moles/liter, based on halogen atoms. In the process of this invention, however, the preferred critical range of ratios of bromide atoms to metal atoms must be maintained as discussed herein to achieve the superior results.

The active catalytic component is preferably supplied as a catalyst solution. The solution can also include liquid reactants, products and mixtures thereof which function as solvents or reaction media.

The ethylene feedstock is normally charged with equimolar amounts of water, although more or less water may optionally be used.

For example in a batch reactor system when ethylene and carbon monoxide are fed in a stoichiometric excess to water some propionic anhydride may be co-produced with propionic acid. Subsequent addition of water to the reactor system or product during isolation steps will convert the anhydride to acid resulting in a substantially quantitative yield of propionic acid.

The bromide promoted rhodium catalysts of the present invention are characterized by a high degree of specificity for the carbonylation reaction, e.g., the reaction of ethylene with carbon monoxide and water to obtain propionic acid selectively. Such control over the various competing reactions to obtain the carboxylic acid in very high yield selectively is surprising since other Group VIII metal catalysts promoted by halides do not show such specificity. Other Group VIII metal catalysts containing high concentrations of halide promoter, e.g., iron, cobalt, nickel, rhodium with high halide levels, differ from the present catalysts in that they produce a number of oxygenated products such as alcohols, aldehydes, lactones, esters and ketones in addition to carboxylic acid.

For a better understanding of the process of the present invention specific embodiments of the process are presented below. These examples and illustrations are not to be construed in any way as limiting the scope of the invention.

EXAMPLE 1

A batch reactor is charged with the following ingredients: 0.133 grams ($5 \times 10^{-4}$ moles) of a rhodium compound having the formula $RhCl_3 \cdot 3H_2O$, as catalyst precursor; 10.2 ml (0.091 moles) of 48% aqueous hydrogen bromide; 74.8 ml of glacial acetic acid as solvent; the olefin feed, ethylene, is charged to the reactor as a 1:1 molar mixture with carbon monoxide. The atomic ratio of Br/Rh is 182:1.

The reactor is pressurized with the gas blend to a total pressure of 400 psig, (p.press of CO about 160 psi) at 175° C. The reaction is carried out at constant pressure by feeding the gas blend upon demand, from a high pressure reservoir. Reaction time is 3½ hours.

The reaction mixture subsequently analyzed by gas chromatographic technique, yields a solution containing:
- 27.0 wt % propionic acid product
- 3.6 wt % miscellaneous intermediates including bromides
- 69.4 wt % acetic acid solvent The selectivity to propionic acid is greater than 99%. No other organic oxygenated compounds such as alcohols, aldehydes, ketones, lactones, etc., are produced from the olefin feed as determined by gas chromatographic analysis. No substantial amounts of other undesirable by-products such as methane, carbon-dioxide, or higher olefin derivatives and/or higher acids are formed.

The rate of reaction varies somewhat during the reaction time in the batch system due to the change in reactant concentrations. However, it has been found that the total gas consumption measured by decrease in pressure of the feed reservoir during the 3½ hour reaction (time is held constant for purposes of comparison) is an excellent representation of catalyst system reactivity. In the examples which follow this gas consumption is expressed in terms of total amount of gas feed mixture consumed at constant reaction time, i.e., $\Delta$ psi/3½ hours. For the 182:1 halide/metal atomic ratio of this example the $\Delta$ psi/3½ hours was 2800 psig.

From the gas chromatographic analysis and isolation of product the yield of propionic acid was 0.42 moles. Since 0.091 moles of bromide and 0.0005 moles of rhodium were used as catalyst the turnover of bromide and rhodium to produce propionic acid were 4.6 and 840 respectively. The fact that the bromide utilization, e.g. catalytic turnover, was over 4 in this instance and even higher in other examples and that the rhodium utilization was over 800 proves that the reaction is definitely catalytic with respect to both the rhodium and bromide components.

In this and subsequent examples reaction rates have been maintained slow and conversion low in order to more clearly demonstrate the concept of critical ratio.

EXAMPLES 2 – 8

Using similar experimental conditions as in Example 1, except varying catalyst components, i.e., rhodium and/or bromide components including the atomic ratio of bromide to rhodium the following results were obtained in the synthesis of propionic acid from ethylene.

TABLE I

These results show the marked reactivity and specificity for propionic acid production at significantly mild partial pressures of CO when employing ratios of bromide/Rh within the critical range described herein (i.e. 40/1 to 350/1).

The results demonstrate that an optimum reactivity and also production of propionic acid occurs, within the same critical range of bromide/Rh ratios.

The results also demonstrate that the production of propionic acid is catalytic in both the rhodium and bromide components within the critical range of bromide/rhodium atomic ratios taught herein. At ratios both higher (e.g. Example 8 Br/Rh = 400) and lower (e.g. Example 2 Br/Rh = 10) than this critical range the carbonylation reaction is not catalytic in the bromide component (Bromide Utilization 0.0 in Example 2 and 0.6 in Example 8).

The concept of critical ratios of bromide/rhodium in the catalyst system of this invention is graphically demonstrated in FIG. 1 using the data from Table I above for the parameters of Bromide Utilization (i.e. moles of propionic acid produced/atom of bromide) vs Bromide/Rhodium atomic ratio.

TABLE 1

| | Run conditions: | Rhodium Component $5 \times 10^{-3}$M, Reactor Pressure 400 psig total (p. press CO about 175 psi) Olefin Feed - Ethylene, Total Volume Charged-85 ml Reaction Time - 3½ hours at 175° C | | | |
|---|---|---|---|---|---|
| Example | Catalyst Components Rhodium & Bromide | Atomic Ratio Br/Rh | Reactivity[a] $\Delta$psi | Propionic Acid[b,c] Production | Bromide[d] Utilization |
| 1 | $RhCl_3 \cdot 3H_2O$ HBr | 182 | 2800 | 27.0 | 4.6 |
| 2 | $RhCl_3 \cdot 3H_2O$ Ethyl Bromide | 10 | No reaction | 0. | 0. |
| 3 | $RhCl_3 \cdot 3H_2O$ HBr | 90 | 950 | 12. | 3.6 |

TABLE 1-continued

Run conditions: Rhodium Component 5 × 10⁻³M, Reactor Pressure 400 psig total
(p. press CO about 175 psi)
Olefin Feed - Ethylene, Total Volume Charged-85 ml
Reaction Time - 3½ hours at 175° C

| Example | Catalyst Components Rhodium & Bromide | Atomic Ratio Br/Rh | Reactivity[a] Δpsi | Propionic Acid[b,c] Production | Bromide[d] Utilization |
|---|---|---|---|---|---|
| 4 | RhCl₃ . 3H₂O HBr | 140 | 2410 | 27.1 | 5.6 |
| 5 | RhCl₃ . 3H₂O Ethyl Bromide | 140 | 850 | 11.6 | 2.3 |
| 6 | Rh(Q₃P)₂COCl HBr | 182 | 3440 | 26.3 | 4.0 |
| 7 | RhCl₃ . 3H₂O Ethyl Bromide HBr | 270 | 3220 | 26.4 | 2.6 |
| 8 | RhCl₃ . 3H₂O Ethyl Bromide | 400 | 610 | 8.8 | 0.6 |

[a]Total gas consumption in standard 3½ hour run
[b]Propionic Acid Production equals wt % in final reaction solution by GC analysis
[c]Selectivity to propionic acid >98% in all cases as determined by gas chromatographic analysis of reaction product mixture.
[d]Moles of propionic acid produced per atom of bromine. Reaction catalytic in bromide only if Bromide Utilization greater than 1.0
(e.g. catalytic for Examples 3–7), less than stoichiometric in bromide for Examples 2 and 8.

Attention is directed to the zone outside of the critical bromide/rhodium ratio. In this zone (shown as cross-hatched in FIG. 1) the reaction is not catalytic in bromide since the bromide utilization is less than 1.0.

For other operating conditions and catalyst concentrations (for example at a rhodium concentration 2×10⁻³M) the critical ratio defined herein is also found to be applicable.

EXAMPLE 9

The reactor system of Example 1 is charged with a longer chain olefin feed stock, hexene-1, at similar reaction conditions as shown below. The results compared with those of Table I demonstrate that the concept of critical ratios of Br/Rh catalyst components is uniquely applicable to the synthesis of propionic acid from ethylene. Comparable high reactivity to carboxylic acid is not attained, relative to the previous ethylene examples when employing hexene-1. Even employing significantly higher partial pressure of carbon monoxide (2 to 3 fold greater) does not enhance the carboxylation reaction when higher olefins are employed with catalyst systems based upon the critical compositions discussed herein.

TABLE 2

Run Conditions: Rhodium Component 5 × 10⁻³M,
Reactor Pressure
700 psig total (p.press, CO about 540 psi),
Substrate is Hexene-1, Total Volume
Charged-100 ml
Reaction time - 3½ hours at 175° C.

| Example | Catalyst Components Rhodium & Bromide | Atomic Ratio Br/Rh | Reactivity[a] | C₇Acid Production[b] |
|---|---|---|---|---|
| 9 | RhCl₃ . 3H₂O HBr | 55:1 | NR[c] | None |

[a]Total gas consumption in standard 3½ hour run.
[b]C₇Acid Production equals wt % in final reaction solution by GC analysis.
[c]NR equals No Reaction.

What is claimed is:

1. A one-step process for the preparation of propionic acid which comprises reacting ethylene with carbon monoxide and water at a temperature of 50° to 300° C and a partial pressure of carbon monoxide of from 1 to 1500 psia in the presence of catalytic proportions of each of:
   1. a rhodium component;
   2. a bromide component, wherein the range of atomic ratios of said bromide to rhodium is from 40:1 to 350:1, and the process is catalytic both with respect to the rhodium and the bromide.

2. A one-step process for the preparation of propionic acid which comprises reacting ethylene with carbon monoxide and water at a temperature of 50° to 300° C and a partial pressure of carbon monoxide of from 1 to 1500 psia in the presence of catalytic proportions of each of:
   1. a rhodium component;
   2. a bromide component, and the process is catalytic both with respect to the rhodium and the bromide, wherein the range of atomic ratios of said bromide to rhodium is from 40:1 to 350:1, the said catalyst system existing as an aqueous solution of a carboxylic acid having from 2 to 20 carbon atoms, the said aqueous solution containing from 1 to 25% by weight of water.

3. A process as in claim 2 in which the catalyst is employed as an aqueous solution of propionic acid, the said aqueous solution containing from 1 to 25% by weight of water.

4. A process as in claim 1 in which the temperature is from 125° to 225° C.

5. A process as in claim 1 in which the partial pressure of carbon monoxide is from 25 psia to 500 psia.

6. A process as in claim 2 in which the partial pressure of carbon monoxide is from 25 psia to 500 psia.

7. A one-step process for the preparation of propionic acid which comprises reacting ethylene with carbon monoxide and water at a temperature of 50° to 300° C and a partial pressure of carbon monoxide of from 1 to 1500 psia in the presence of
   1. a rhodium component;
   2. a bromide component, wherein the range of atomic ratios of said bromide to rhodium is from 80:1 to 250:1.

8. A one-step process for the preparation of propionic acid which comprises reacting ethylene with carbon monoxide and water at a temperature of 50° to 300° C and a partial pressure of carbon monoxide of from 1 to 1500 psia in the presence of
   1. a rhodium component;
   2. an ethyl bromide component, wherein the range of atomic ratios of said bromide to rhodium is from 80:1 to 250:1 the said catalyst system existing as an aqueous solution of a carboxylic acid having from 2 to 20 carbon atoms, the said aqueous solution containing from 1 to 25% by weight of water.

* * * * *